US00RE36081E

United States Patent [19]

Kent

[11] E Patent Number: Re. 36,081

[45] Reissued Date of Patent: Feb. 9, 1999

[54] BROMELIAD PLANT NAMED 'GUZ 211'

[75] Inventor: Jeffrey C. Kent, Vista, Calif.

[73] Assignee: Kent's Bromeliad Nursery, Inc., Vista, Calif.

[21] Appl. No.: 837,149

[22] Filed: Apr. 14, 1997

Related U.S. Patent Documents

Reissue of:

[64] Patent No.: Plant 9,475
Issued: Mar. 12, 1996
Appl. No.: 323,726
Filed: Oct. 19, 1994

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

| | | | |
|---|---|---|---|
| P.P. 7,471 | 3/1991 | Bak et al. | Plt./88.8 |
| P.P. 8,613 | 2/1994 | Pielers et al. | Plt./88.8 |
| P.P. 8,715 | 5/1994 | Hill | Plt./88.8 |

*Primary Examiner*—James R. Feyrer
*Attorney, Agent, or Firm*—James A. Lucas

[57] ABSTRACT

A cross of Guzmania 'Lingulata' and 'Wittmackii' which differs from other crosses of the same in the fact that the bract's coloration goes further down the peduncle, is bi-colored, and a carmine 31+ color with a suffusion of rose 38+, the habit being lax, except for the inflorescence.

2 Drawing Sheets

Matter enclosed in heavy brackets [ ] appears in the original patent but forms no part of this reissue specification; matter printed in italics indicates the additions made by reissue.

This invention relates to bromeliads and primarily to a bromeliad which is the product of crossing a seed parent Guzmania lingulata 'Panama' (unpatented) with the pollen parent Guzmania wittmackii 'Pink', likewise unpatented.

In point of fact the plant is the product of a long period of development which I have conducted over many years in the effort to provide plants of the bromeliad family which are commercially desirable and healthy as far as being able to ship and display.

As a result of this program I have developed the instant variety and selected the same from a cultivated area in a large planting of Guzmania as indicated herein and this particular plant, I denominate as 'Guz 211' for commercial use.

I have caused the plant to be reproduced by tissue cuture in the neighborhood of Rancho Santa Fe, Calif., and found that over time as a result of such asexual reproduction and continuing reproduction the plant holds true from generation to generation.

In describing the parentage, the seed parent G. lingulata 'Panama' provides leaves which are linear, medium, accuminate, and of medium green color. It includes floral bracts which are linear, acute, with scarlet flowers. The bracts are white, medium, pointed, the petals scarcely open after anthesis.

Turning to the matter of the pollen parent, which is denominated as G. wittmackii 'Pink' unpatented as before indicated, with linear leaves, that are long, accuminate, medium to light green. They are somewhat recurved and the floral bracts are rust color. The flowers are white, long, pointed and appressed, circinnate.

Generally speaking, this hybrid of G. lingulata×G. wittmackii is distinguished from other plants resulting from crosses from different members of the parental species by expressing an attractive and intense coloration of bright red tones which extend throughout the inflorescence and downwardly on the spike/main stem of specimens of this plant. Bract coloration is a pleasing blend of bright tones of Carmine 31+ with a suffusion of Rose 38+ that follows a general pattern of brighter colors being presented on the outwardly extending portions of the bracts and deeper tones occupying the basal portions of the bracts. While modern hybrids between these two species are similar in phenotype, 'Guz 211' can be readily distinguished from other market available interspecific hybrids of the same parent species. When compared to 'Rana' (U.S. Plant Pat. No. 7,471) and 'Guinn' (U.S. Plant Pat. No. 8,715), 'Guz-211' produces a shorter, more compact plant, and has a flower spike which is darker in hue. 'Guz-211' also has a more extensively colored spike with less green on the lower bract tips and red coloration extending lower on the spike when compared to each of these two comparison plants. This plant produces specimens which are less squat than those produced by 'Red Star'; and shows fewer white tips on terminal bracts, and has bracts of more uniform shape and size from top to bottom of the spike. Basal bracts of 'Guz-211' are longer than those formed by 'Red Star', and 'Red Star' has darker, more substantial leaves than 'Guz-211'.

The habit of 'Guz 211' is fairly typical of market available plants of this hybrid class, but has highly desirable characteristics not present in other, similar plants. While gently arched at maturity, the leaves of this plant remain ascending and strong in appearance with the development of the inflorescence. The advance from leaf to flower bract shape and attitude is more gradual with 'Guz 211', when compared to other similarly colored hybrids from similar genetic background, resulting in finished specimens which have smoother profiles than other market available varieties. Accordingly, while the general appearance and coloration of hybrids from the parent species have been selected from among the widely ranging myriad of bract colors resulting from such crosses, the plant of this invention stands out among the known varieties selected and introduced from crosses of the same parent species.

This range of color affects the color of the hybrids, striking variations being found within the same crossing.

BRIEF DESCRIPTION OF THE DRAWING

I append hereto a color illustration of a typical plant of my new variety, primarily the flower portion thereof, which is the most distinctive part of the plant and is shown as near the actual colors of the plant as photo reproduction of this kind can depict.

Color values presented in this disclosure were taken from The Horticultural Color Guide as presented in Exotica. Such color definitions are based on the Dictionary of Color by Maerz & Paul. Color definitions of ordinary meaning are presented where appropriate and properly descriptive.

In order to point out more specifically the most notable aspects and novel characteristics of the plant of this invention, as set forth above, the following detailed botanical description presents the general as well as the specific characteristics of 'Guz 211'.

PLANT

General characteristics:

Type.—Monocot, perennial.

Habit.—Single stem, whorled and closely spaced ascending linear, strap-like leaves with acuminate terminals, typical of hybrids of G. lingulata×G. wittmackii. Lower leaves may droop with age if plant is not timely induced to flower. Terminal portions of most mature leaves may droop in a graceful arch.

Hardiness.—Tender, tropical.

Size.—About 23 to 24 inches, or more, in width, with the ultimate height determined by the timing of gas induction of blooming. Plant height for optimum marketing is about 18 to 19inches, including the inflorescence.

Shape.—Normally mounded, generally typical of plants of the genus.

Density.—Leaf spacing is typically close to very close, and typical of hybrids of the market class. Leaf spacing and internode length may increase with low light conditions or when too much nitrogen fertilizer is applied.

Leaves:

Length.—20" to 21".

Width.—1". Large for size of plant linear, acuminate, acutely pointed, medium to thin, ivy green (70), and smooth. Young leaves ivy green (70) flushed with amethyst (46), particularly the venation (obverse and reverse), this disappearing with the formation of each successive leaf.

Margin.—Smooth.

Petiole.—Apetiolate.

Inflorescence: Unbranched spike, apical bractlets carmine (31+) and tipped white in color.

Flower buds: Tender, medium, long to medium in width, pointed, and appressed, 3/16"×1½.

Bracts: Linear acute 7"×1½" at the base of inflorescence decreasing to 3"×1" at apex. Somewhat conduplicate and dropping at the base to more conduplicate and ascending at the apex. Obverse and reverse of upper bracts carmine (31+) in color, obverse and reverse of lower bracts carmine (31+) and blending to rose (38) at the midsection, and tipped with ivy green (70) as the leaves with less green and rose (38) toward the apex. The colors become paler after anthesis.

Flowers: Cylindrical corolla, white at anthesis, with petals scarcely opening, Glomerate, sepals and petals, acutely pointed, 3/16"×1½".

Reproductive organs: Six stamen, two joined to each petal ¼ of the distance from the base, stigmata white, sterile $F^1$ hybrid.

I claim:

1. A new and distinct Guzmania plant, named 'Guz 211', as illustrated and described, particularly distinguished by having a more extensively colored spike and by having inflorescence coloration made up of an unusual carmine interestingly suffused with rose.

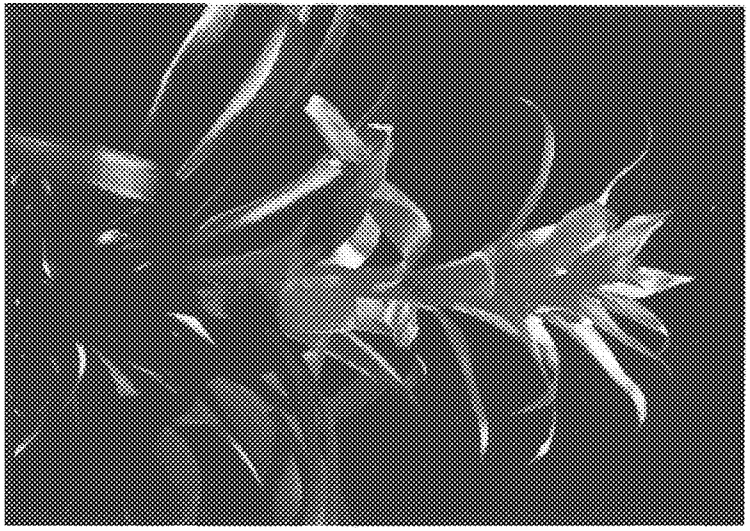

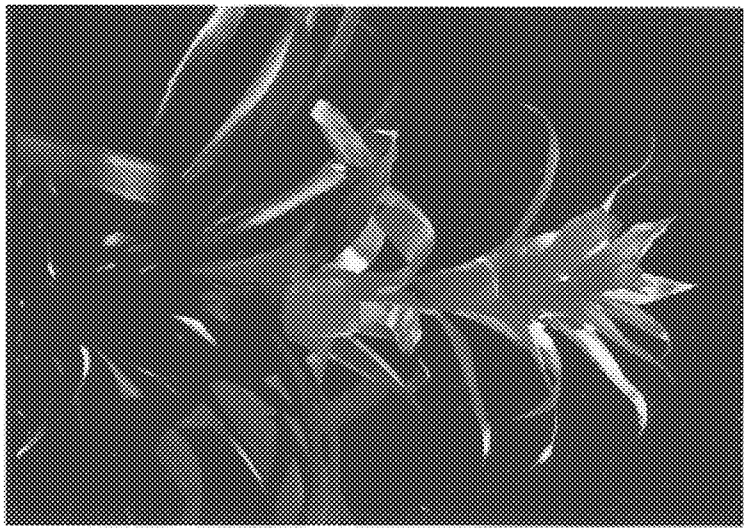

* * * * *